(12) United States Patent
Wen et al.

(10) Patent No.: US 11,480,561 B2
(45) Date of Patent: Oct. 25, 2022

(54) SYSTEMS AND METHODS FOR MONITORING IMMUNOTHERAPY TOXICITY

(71) Applicant: Cardiac Pacemakers, Inc., St. Paul, MN (US)

(72) Inventors: Gezheng Wen, Shoreview, MN (US); Qi An, Blaine, MN (US); Pramodsingh Hirasingh Thakur, Woodbury, MN (US); Deepa Mahajan, North Oaks, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 346 days.

(21) Appl. No.: 16/518,621

(22) Filed: Jul. 22, 2019

(65) Prior Publication Data
US 2020/0057050 A1    Feb. 20, 2020

Related U.S. Application Data

(60) Provisional application No. 62/718,733, filed on Aug. 14, 2018.

(51) Int. Cl.
*A61B 5/0205* (2006.01)
*G01N 33/50* (2006.01)

(52) U.S. Cl.
CPC ....... *G01N 33/5014* (2013.01); *A61B 5/0205* (2013.01); *G01N 33/505* (2013.01); *G01N 33/5088* (2013.01); *G01N 2500/10* (2013.01); *G01N 2800/52* (2013.01)

(58) Field of Classification Search
CPC ............. G01N 33/5014; G01N 33/505; G01N 33/5088; G01N 2500/10; G01N 2800/52; A61B 5/0205
See application file for complete search history.

(56) References Cited

U.S. PATENT DOCUMENTS

| 4,003,379 A | 1/1977 | Ellinwood, Jr. |
| 9,622,664 B2 | 4/2017 | An et al. |
| 2007/0299477 A1* | 12/2007 | Kleckner ............. A61N 1/3627 607/9 |

(Continued)

FOREIGN PATENT DOCUMENTS

| WO | WO-2019200251 A1 * | 10/2019 | ........... A61K 31/711 |
| WO | WO-2020036706 A1 | 2/2020 | |

OTHER PUBLICATIONS

Hunter, J.D., et al., "Sepsis and the heart", British Journal of Anaesthesia 104 (1): 3-11 (2010).

(Continued)

*Primary Examiner* — Ankit D Tejani
*Assistant Examiner* — Joshua Brendon Solomon
(74) *Attorney, Agent, or Firm* — Schwegman Lundberg & Woessner, P.A.

(57) ABSTRACT

Systems, devices, and methods for monitoring and assessing immunotherapy toxicity are discussed. An exemplary system receives physiologic information from a patient using an ambulatory medical device. In response to an immunotherapy such as CAR T-cell therapy, the system determines a toxicity indication using the received physiologic information. A therapy can be initiated or adjusted using the toxicity indication.

20 Claims, 5 Drawing Sheets

(56) References Cited

U.S. PATENT DOCUMENTS

| | | | | |
|---|---|---|---|---|
| 2011/0312907 A1* | 12/2011 | Hayden | ............... | C12Q 1/6876 |
| | | | | 250/282 |
| 2016/0220821 A1* | 8/2016 | O'Connell | ........ | A61M 5/14276 |
| 2016/0224754 A1* | 8/2016 | Hann | ..................... | G16H 50/30 |
| 2017/0367604 A1* | 12/2017 | Spangler | ................ | G16H 50/30 |
| 2017/0367605 A9* | 12/2017 | Saba | ...................... | A61B 5/363 |
| 2018/0028761 A1 | 2/2018 | Anand et al. | | |
| 2021/0187004 A1* | 6/2021 | McMahon | ........... | G01N 33/574 |

OTHER PUBLICATIONS

"Chimeric Antigen Receptor (CAR) Cell Therapy Toxicity Assessment and Management—Pediatric", MD Anderson Cancer Center, <https://www.mdanderson.org/documents/for-physicians/algorithms/clinical-management/clin-management-cytokine-release-pedi-web-algorithm.pdf>, (Jan. 30, 2018).
"International Application Serial No. PCT/US2019/042837, International Preliminary Report on Patentability dated Feb. 25, 2021", 9 pgs.
"International Application Serial No. PCT/US2019/042837, International Search Report dated Oct. 25, 2019", 5 pgs.
"International Application Serial No. PCT/US2019/042837, Written Opinion dated Oct. 25, 2019", 7 pgs.
Sattva, S Neelapu, et al., "Chimeric antigen receptor T-cell therapy-assessment and management of toxicides", Nature Reviews Clinical Oncology, vol. 15, No. 1, (Sep. 19, 2017), 47-62 pgs.

\* cited by examiner

SYSTEMS AND METHODS FOR MONITORING IMMUNOTHERAPY TOXICITY

CLAIM OF PRIORITY

This application claims the benefit of priority under 35 U.S.C. § 119(e) of U.S. Provisional Patent Application Ser. No. 62/718,733, filed on Aug. 1, 2018, which is herein incorporated by reference in its entirety.

TECHNICAL FIELD

This document relates generally to medical devices, and more particularly, but not by way of limitation, to systems, devices, sensors, and methods for monitoring immunotherapy toxicity.

BACKGROUND

The immune system is the body's defense against infection and cancer. A major portion of the immune system is comprised of lymphocytes, a subtype of white blood cells. There are three major types of lymphocytes that have action against cancerous tumors: B cells to make antibodies to fight infection, T cells to help B cells to make antibodies to fight infection and directly kill infected cells in the body, and natural killer (NK) cells that also attack infected cells and eliminate viruses. Normally, T-cells have a direct killing action on cancer cells. However, cancer cells can evade the T cells. The T-cells can become less effective, have low proliferation, and become less effective in recognizing cancer cells.

Immunotherapy is a type of treatment that utilizes the body's own immune system to fight cancer. Immunotherapy can improve the body's ability to detect and kill cancer cells. Chimeric antigen receptor (CAR) T-cell therapy is a form of immunotherapy that can help boost the cancer-killing effects of the T cells. The CAR T-cell therapy involves separating a patient's T cells and genetically engineering the T cells to express a CAR to target the tumor antigen. The re-engineered CAR T-cell is then re-infused back into the patient, where they continue to multiply, seek out, redirects the T cells to attack the cancerous cells. In some patients, the CAR T-cells remain in the body after infusion and can continue to function for an extended period of time.

CAR T-cell therapy may be used treat various cancer patient, such as adult patients with relapsed or refractory large B-cell lymphomas. Leukemias, such as acute lymphoblastic leukemia, have also shown extended remissions in CAR T-cell therapy. Evolving research has been done to direct CAR T-cells to treat liver cancer, breast cancer, lung cancer, pancreatic cancer, among others.

Immunotherapy such as CAR T-cell therapy may cause an adverse effect known as cytokine release syndrome (CRS), which is a form of systemic inflammatory response. The CRS may also arise as a complication of some diseases or infections. The CRS occurs when a large number of white blood cells are activated, and rapidly release inflammatory cytokines into the blood, which in turn activate yet more white blood cells. Cytokines are immune substances that have many different actions in the body. When cytokines are released into the circulation, they may cause multi-organ toxicity. Systemic symptoms such as fever, nausea, chills, hypotension, hypoxia, tachycardia, asthenia, headache, rash, scratchy throat, and dyspnea can result. In most patients, the symptoms are mild to moderate in severity and are managed easily. However, some patients may experience severe, life-threatening reactions that result from massive release of cytokines. Severe reactions occur more commonly during the first infusion in patients with hematologic malignancies who have not received prior chemotherapy; severe reactions are marked by their rapid onset and the acuity of associated symptoms. Massive cytokine release is an oncologic emergency, and special precautions must be taken to prevent life-threatening complications.

Timely and accurate detection of CRS or other inflammatory response to immunotherapy such as CART T-cell therapy, particularly in an ambulatory patient, may allow appropriate therapy titration and thus help prevent adverse patient outcome.

SUMMARY

Toxicity assessment and management of patients suffering from immunotherapy toxicity can be costly and take significantly amount of time and resources. Patients receiving CAR T-cell therapy typically require frequent multi-principle preventive and supportive care interventions, such as vital sign assessment and intravenous fluid injections every 4-6 hours. Such patients need be hospitalized and monitored for at least seven days after CAR T-cell infusion. Most patients are admitted for several weeks (e.g., a 4-week monitoring period). Many patients are often re-admitted, especially during the first 30 days after discharge. Therefore, toxicity assessment and management post CAR T-cell therapy can be a high clinical and financial burden in cancer patient care.

This document discusses, among other things, systems and methods to receive physiologic information from a patient using an ambulatory medical device, and to determine, in response to an immunotherapy, such as CAR T-cell therapy, a toxicity indication using the received physiologic information. In an example, the immunotherapy toxicity may be monitored continuously using multiple wearable or implanted sensors. The multi-sensor approach discussed herein may lead to more efficient post-immunotherapy toxicity management, improve patient outcome, and reduce overall healthcare cost.

Example 1 is a system comprising an ambulatory medical device configured to receive physiologic information from a patient receiving immunotherapy, and an assessment circuit configured to determine (e.g., in response to an immunotherapy) a toxicity indication associated with the immunotherapy using the received physiologic information. In an example, the immunotherapy can optionally include a chimeric antigen receptor (CAR) T-cell therapy.

In Example 2, the subject matter of Example 1 optionally includes a drug delivery system configured to control delivery of the immunotherapy to the patient according to a delivery parameter. The immunotherapy may include a chimeric antigen receptor (CAR) T-cell therapy, and the assessment circuit may be configured to determine an optimized delivery parameter for delivering the immunotherapy using the determined toxicity indication.

In Example 3, the subject matter of Example 2 optionally includes the drug delivery system configured to control delivery of an anti-toxicity drug to the patient according to a delivery parameter, and the assessment circuit that may be configured to determine an optimized delivery parameter for delivering the anti-toxicity drug using the determined toxicity indication.

In Example 4, the subject matter of any one or more of Examples 2-3 optionally includes the delivery parameter that may include at least one of a dosage, a timing, or a drug.

In Example 5, the subject matter of any one or more of Examples 1-4 optionally includes the assessment circuit configured to provide an alert to a user using the determined toxicity indication.

In Example 6, the subject matter of any one or more of Examples 1-5 optionally includes a therapy circuit configured to control a therapy to the patient according to a therapy parameter. The assessment circuit may be configured to adjust the therapy parameter using the determined toxicity indication.

In Example 7, the subject matter of Example 6 optionally includes the assessment circuit configured to: determine an acute toxicity index for the patient using the received physiologic information; compare the determined acute toxicity index to a threshold; and in response to the determined acute toxicity index exceeding the threshold, adjust the therapy parameter using the determined acute toxicity index.

In Example 8, the subject matter of any one or more of Examples 1-7 optionally includes the ambulatory medical device that may include a cardiac sensor configured to receive cardiac electrical or mechanical information of the patient. The assessment circuit may be configured to determine the toxicity indication using the received cardiac electrical or mechanical information.

In Example 9, the subject matter of Example 8 optionally includes the cardiac sensor that may include electrodes configured to sense cardiac electrical information including one or more of a heart rate, a heart rate variability, a Q-T interval, or a cardiac arrhythmia, and the assessment circuit configured to determine the toxicity indication using the sensed cardiac electrical information.

In Example 10, the subject matter of any one or more of Examples 1-9 optionally includes the ambulatory medical device that may include a heart sound sensor configured to receive heart sound information of the patient. The assessment circuit may be configured to determine the toxicity indication using the receive heart sound information.

In Example 11, the subject matter of Example 10 optionally includes the assessment circuit configured to determine the toxicity indication using one or more of a decrease in first heart sound (S1) amplitude, a decrease in second heart sound (S2) amplitude, or an increase in third (S3) or fourth (S4) heart sound amplitude.

In Example 12, the subject matter of Example 11 optionally includes the assessment circuit configured to determine the toxicity indication using an increase in a systolic time interval.

In Example 13, the subject matter of any one or more of Examples 1-12 optionally includes the ambulatory medical device that may include a respiratory sensor configured to receive respiration information of the patient. The assessment circuit may be configured to determine the toxicity indication using the received respiration information.

In Example 14, the subject matter of any one or more of Examples 1-13 optionally includes the ambulatory medical device that may include a chemical sensor configured to receive blood chemical information. The assessment circuit may be configured to detect renal or hepatic dysfunction, and to determine the toxicity indication using the detected renal or hepatic dysfunction.

In Example 15, the subject matter of any one or more of Examples 1-14 optionally includes the assessment circuit configured to: generate a composite risk score using the received physiologic information respectively received from two or more physiologic sensors; and determine the toxicity indication using the composite risk score.

Example 16 is a method comprising steps of: delivering an immunotherapy to a patient; receiving physiologic information from the patient; and determining a toxicity indication associated with the immunotherapy using the received physiologic information.

In Example 17, the subject matter of Example 16 optionally includes determining an optimized delivery parameter for delivering the immunotherapy using the determined toxicity indication, and delivering the immunotherapy to the patient according to the determined optimized delivery parameter.

In Example 18, the subject matter of Example 17 optionally includes the delivery parameter that may include at least one of a dosage, a timing, or a drug.

In Example 19, the subject matter of any one or more of Examples 16-18 optionally includes comprising initiating or adjusting an electrostimulation therapy using the determined toxicity indication.

In Example 20, the subject matter of any one or more of Examples 16-19 optionally includes: determining an acute toxicity index for the patient using the received physiologic information; comparing the determined acute toxicity index to a threshold; and in response to the determined acute toxicity index exceeding the threshold, adjusting a therapy parameter using the determined acute toxicity index.

In Example 21, the subject matter of any one or more of Examples 16-20 optionally includes the received physiologic information that may include one or more of: cardiac information; heart sound information; respiration information; body temperature information; blood oxygen saturation information; or blood chemical information.

In Example 22, the subject matter of any one or more of Examples 16-21 optionally includes: generating a composite risk score using the received physiologic information respectively received from two or more physiologic sensors; and determining the toxicity indication using the composite risk score.

This summary is intended to provide an overview of subject matter of the present patent application. It is not intended to provide an exclusive or exhaustive explanation of the disclosure. The detailed description is included to provide further information about the present patent application. Other aspects of the disclosure will be apparent to persons skilled in the art upon reading and understanding the following detailed description and viewing the drawings that form a part thereof, each of which are not to be taken in a limiting sense.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

DETAILED DESCRIPTION

The present inventor has recognized, among other things, that continuous monitoring, such as through an ambulatory medical device, including a wearable or implantable sensor, can enable early detection and better management of toxicity of immunotherapy, such as CAR T-cell therapy, in cancer patients, potentially significantly expanding insertable cardiac monitor (ICM) or other ambulatory medical device indications.

Immune-mediated toxicities in cancer patients may include one or more of cardiac, respiratory, neurologic, hematologic, gastrointestinal, hepatic, or renal toxicities, causing multi-organ inflammatory responses and toxic damages. Immunotherapy toxicity can be an acute reaction that appears within several hours, days, or weeks (e.g., 3-4 weeks) after patient receiving the immunotherapy. Early recognition of immunotherapy toxicity is critical for treatment. If detected, immunotherapy toxicity can be managed or reversed, such as using cardioprotective drugs (e.g., beta-blockers or ace-inhibitors, etc.) for lessening or reversing cardiotoxicity. Conventionally, immunotherapy toxicity assessment and management is single, intermittent assessment and requires to be tested in a clinical setting. This may be undesirable for ambulatory patients and those in an immunocompromised state and require continuous monitoring toxicity assessment. If immunotherapy toxicity progresses without timely detection or appropriate treatment, it can become irreversible, leading to patient death.

In an example, one or more existing ambulatory medical device sensors can be used to detect early subclinical manifestations of immunotherapy toxicity, during or after an immunotherapy, such as to pre-screen for further medical intervention or therapy optimization (e.g., drug titration or timing, etc.). Such advancements can provide for early detection of treatable conditions, in certain examples providing additional use for existing sensors, reducing sensor cost, and enabling earlier intervention, improving patient outcomes, and reducing overall medical system costs. The systems and methods described herein, in certain examples, represent an improved form of immunotherapy toxicity detection and patient intervention over existing techniques. In certain examples, patients can be monitored, and the patient, caregiver, clinician, or one or more other system or user can be alerted to a change in patient condition indicative of immunotherapy toxicity, or a likelihood of immunotherapy toxicity. In other examples, the systems and methods described herein can provide a recommended intervention or therapy optimization (e.g., dosage or timing change, change in prescribed drug, etc.), or can directly provide or alter a therapy to the patient.

Figure 1:
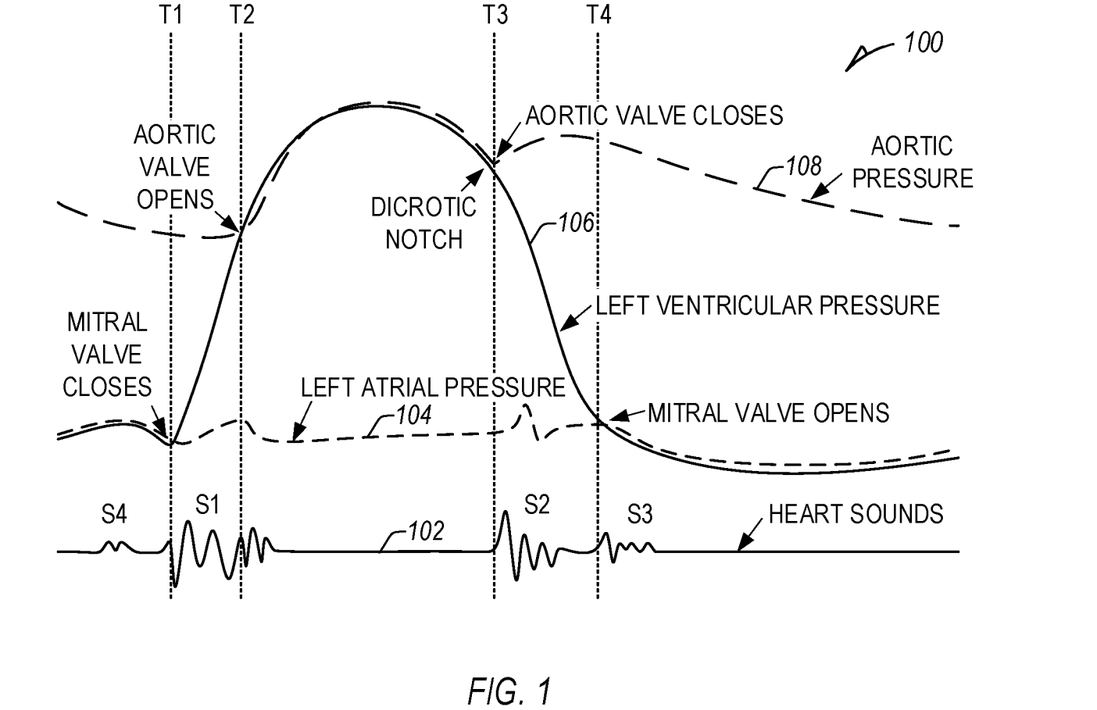
FIG. 1 illustrates an example of multiple physiologic parameters and timing relationship therebetween.

FIG. 1 illustrates an exemplary relationship 100 among various physiologic parameters measured from a subject. Some or all of the physiologic parameters shown in FIG. 1 may be monitored using sensors, such as ambulatory sensors, during and after patient receiving immunotherapy, and be used to detect and assess degree of toxicity of immunotherapy. By way of example and not limitation, the physiologic parameters heart sounds 102, including first, second, third, and fourth heart sounds (S1, S2, S3, and S4), left atrial pressure 104, left ventricular pressure 106, and aortic pressure 108.

At a first time (T1), a mitral valve closes, marking a rise in left ventricular pressure 106, and the start of the first heart sound (S1) and systole, or ventricular contraction. At a second time (T2), an aortic valve opens, marking a rise in aortic pressure 108 and continuing S1. S1 is caused by closure of the atrioventricular (AV) valves, including the mitral and tricuspid valves, and can be used to monitor heart contractility.

At a third time (T3), an aortic valve closes, causing a dicrotic notch in the aortic pressure 108 and the second heart sound (S2), and marking the end of systole, or ventricular contraction, and the beginning of diastole, or ventricular relaxation. S2 can be used to monitor blood pressure. At a fourth time (T4), the mitral valve opens, and the left atrial pressure 104 drops. An abrupt halt of early diastolic filling can cause the third heart sound (S3), which can be indicative of (or an early sign of) heart failure (HF). Vibrations due to atrial kick can cause the fourth heart sound (S4), which can be used to monitor ventricular compliance.

Systolic time intervals, such as pre-ejection period (PEP) or left ventricular ejection time (LVET) can be indicative of clinically relevant information, including contractility, arrhythmia, Q-T prolongation (with electrogram (EGM) information), etc. The PEP can be measured from a Q wave of an EGM to the time of the aortic valve opening, T2 in FIG. 1. The LVET can include a time between the aortic valve opening, T2, and the aortic valve closing, T3. In other examples, one or more systolic time intervals can be detected and used to detect physiologic information of a patient (e.g., PEP/LVET, one or more mechanical, electrical, or mechanical-electrical time intervals, etc.).

Ambulatory medical devices, including implantable, leadless, or wearable medical devices configured to monitor, detect, or treat various cardiac conditions associated with a reduced ability of a heart to sufficiently deliver blood to a body, such as heart failure (HF), arrhythmias, hypertension, etc. Various ambulatory medical devices can be implanted in a patient's body or otherwise positioned on or about the patient to monitor patient physiologic information, such as heart sounds, respiration (e.g., respiration rate, tidal volume, etc.), impedance (e.g., thoracic impedance), pressure, cardiac activity (e.g., heart rate (HR)), physical activity, posture, or one or more other physiologic parameters of a patient, or to provide electrical stimulation or one or more other therapies or treatments to optimize or control contractions of the heart.

Traditional cardiac rhythm management (CRM) devices, such as pacemakers, defibrillators, or cardiac monitors, include implanted devices (e.g., implantable cardioverter-defibrillators (ICDs), etc.), subcutaneous devices (e.g., subcutaneous ICDs (S-ICDs), etc.), or one or more other devices configured to be implanted within in a chest of a patient, or under the skin of the patient, in certain examples, having one or more leads to position one or more electrodes or other sensors at various locations in the heart, such as in one or more of the atria or ventricles. Separate from, or in addition to, the one or more electrodes or other sensors of the leads, the CRM device can include one or more electrodes or other sensors (e.g., a pressure sensor, an accelerometer, a gyroscope, a microphone, etc.) powered by a power source in the CRM device. The one or more electrodes or other sensors of the leads, the CRM device, or a combination thereof, can be configured detect physiologic information from, or provide one or more therapies or stimulation to, the patient, for example, using one or more stimulation circuits.

Leadless cardiac pacemakers (LCP) include small (e.g., smaller than traditional implantable CRM devices), self-contained devices configured to detect physiologic information from or provide one or more therapies or stimulation to the heart without traditional lead or implantable CRM device complications (e.g., required incision and pocket, complications associated with lead placement, breakage, or migration, etc.). In certain examples, an LCP can have more limited power and processing capabilities than a traditional CRM device; however, multiple LCP devices can be implanted in or about the heart to detect physiologic information from, or provide one or more therapies or stimulation to, one or more chambers of the heart. The multiple LCP devices can communicate between themselves, or one or more other implanted or external devices.

Wearable or external medical sensors or devices can be configured to detect or monitor physiologic information of the patient without required implant or an in-patient procedure for placement, battery replacement, or repair. However, such sensors and devices, in contrast to implantable, subcutaneous, or leadless medical devices, may have reduced patient compliance, increased detection noise, or reduced detection sensitivity.

Determination of one or more patient conditions (e.g., hypertension, HF, etc.), or risk stratification for one or more patient conditions, often requires some initial assessment time to establish a baseline level or condition from one or more sensors or physiologic information from which a detected deviation is indicative of the patient condition, or risk of patient condition or future adverse medical event (e.g., the risk of the patient experiencing a heart failure event (HFE) within a following period, etc.). Changes in physiologic information can be aggregated and weighted based on one or more patient-specific stratifiers. However, such changes and risk stratification are often associated with one or more thresholds, for example, having a clinical sensitivity and specificity across a target population with respect to a specific condition (e.g., HF), etc., and one or more specific time periods, such as daily values, short-term averages (e.g., daily values aggregated over a number of days), long-term averages (e.g., daily values aggregated over a number of short-term periods or a greater number of days (sometimes different days than used for the short-term average)), etc.

For example, a multisensor algorithm has been demonstrated to predict HF events in patients with a high sensitivity and low false positive rate using physiologic information detected from one or more implanted or ambulatory medical devices. In other examples, such algorithm can be applied to one or more other medical events, such as hypertension or one or more conditions associated with hypertension, etc. The multisensor algorithm can determine a composite physiologic parameter using one or more of the following physiologic information: heart sounds (e.g., a first heart sound (S1), a second heart sound (S2), a third heart sound (S3), a fourth heart sound (S4), heart-sounds related time intervals, etc.), thoracic impedance (TI), respiratory rate (RR), rapid shallow breathing index (RSBI), heart rate (HR) (e.g., nighttime HR), activity, posture, cardiac activity, pressure, etc.

In certain examples, such multisensor algorithm can be adjusted using a determined patient risk level (e.g., a stratifier). The combination of or weight of respective primary and secondary sensors used to determine the composite physiologic parameter can be adjusted using the determined patient risk level. For example, if the determined patient risk level indicates a low risk of a worsening physiologic condition, the composite physiologic parameter can be determined using one or more primary sensors (and not one or more secondary sensors). If the determined patient risk level indicates a medium or high risk of worsening heart failure, the composite physiologic parameter can be determined using the primary sensors and a combination of the secondary sensors, depending on the determined patient risk level. In an example, the multisensory algorithm can determine an indication of immunotherapy toxicity, and to provide an alert, a recommended intervention or change in parameter or therapy, or to directly change or provide a therapy to the patient.

In an example, S1 amplitude can be a marker of contractile function (e.g., a decrease in S1 amplitude, or a decrease in the change of S1 amplitude, can be indicative of reduced contractility or contractile function, and vice versa, etc.). Systolic time intervals (e.g., PEP, PEP/LVET, etc.) can also be indicative of contractile function (e.g., an increase in PEP or PEP/LVET can be indicative of a decrease in contractility). Low contractility, or a decrease in contractility, can be indicative of a decrease in cardiac function, and accordingly, in combination with immunotherapy for cancer treatment, an increased likelihood of immunotherapy toxicity. For example, cardiotoxicity resulted from CAR T-cell therapy may decrease cardiac contractility, and result in reduced ejection fraction, sinus tachycardia and other supraventricular or ventricular arrhythmias, or heart block. Accordingly, a decrease in S1 amplitude and/or an increase in a systolic time interval are early indicators of cardiotoxicity of immunotherapy.

In an example, S2 amplitude can be a marker of afterload changes (e.g., an increase in S2 can be indicative of increased afterload, and a reduction of stroke volume, etc.) As afterload increases, cardiac output decreases. This may be accompanied by hypotension (reduced blood pressure). A decrease in stroke volume, or cardiac output, can be indicative of a decrease in cardiac function, and accordingly, in combination with cancer treatment, an increased likelihood of immunotherapy toxicity. For example, a patient receiving CAR T-cell therapy may develop systemic symptom of hypotension at least due to reduced cardiac output. Accordingly, S2 can be indicative of afterload, stroke volume, cardiac output, or systolic blood pressure, and can be used as an early indicator of immunotherapy toxicity.

In an example, S3 amplitude, thoracic impedance, or respiratory measurements can be used to track fluid or preload changes, and further, can be an early indicator of worsening heart failure (WHF). An increase in S3, S4, or S4/S3 ratio can be indicative of worsening of cardiac diastolic function, which may be associated with lung fluid accumulation. Further, changes in respiratory rate (e.g., median respiratory rate trend (RRT) (minimally impacted by activity or exercise), etc.), tidal volume, rapid shallow breathing index (RSBI), dyspnea, tachypnea, hypoxia, heart rate (e.g., resting heart rate), or combinations thereof, can be indicative of decreased cardiac function (e.g., an increased respiratory rate, tidal volume, or heart rate (e.g., resting heart rate) can be indicative of decreased cardiac output). Immune-mediated respiratory toxicities, secondary to CAR T-cell therapy, may be presented as pulmonary edema, dyspnea, or pneumonitis, which may exacerbate heart failure or other cardiac conditions. Accordingly, S3, thoracic impedance, or directly measured respiratory parameters may be used as an early indicator of immunotherapy toxicity.

In an example, one or more electrical, mechanical, or electrical-mechanical intervals can be used to track cardiac output or one or more other conditions, such as Q-T prolongation, etc., indicative of a decrease in cardiac output. For example, one or more of a Q-T interval, an R-T interval, an R-S2 interval, or one or more other electrical, mechanical, or electrical-mechanical intervals can be indicative of Q-T prolongation (e.g., an increase in one or more of the Q-T, R-T, or R-S2 interval can be indicative of an increase in Q-T prolongation, which can be indicative of arrhythmia, or a decrease in cardiac output, etc.), which, in combination with cancer treatment, can be indicative of an increased likelihood of immunotherapy toxicity.

In an example, one or more ambulatory medical devices can be configured to monitor patient response to a stimulus, such as a prescreening dose of water or saline, to detect patient response. Patients responding abnormally to such stimulus (e.g., water or saline) can be screened for further intervention or continued monitoring. In other examples, separate mechanisms (cause/effect) can be monitored by comparing temporal evolution of sensors (e.g., comparing a rate of S1 change versus intrathoracic impedance (ITTI), etc.), and the temporal evolution of the sensors can be indicative of an increased likelihood of immunotherapy toxicity.

In an example, the systems and methods described herein can be used to adjust or optimize cancer treatment to the patient. In certain examples, cancer treatments may kill cancerous cells or stop or slow the growth of cancerous cells at a moderate to severe impact to patient health. For example, immunotherapy such as CAR T-cell therapy may cause adverse effects of cytokine release syndrome, which is a systemic inflammatory response associated with cardiac, respiratory, neurologic, hematologic, gastrointestinal, hepatic, or renal toxicities. Higher therapy dosages can be better for cancer treatment, but worse inflammatory responses or organ damages. During cancer treatment, adverse cardiac, respiratory, hepatic, or renal impacts may be less weighty than the efficacy of cancer treatment, but only to a point. Currently, ambulatory continuous monitoring and assessment of systematic toxicity is not part of cancer treatment. The systems and methods described herein can be used to monitor toxic effects during or after immunotherapy treatment, to optimize treatment (e.g., infusion, dosage, timing, etc.), in certain examples, increasing the harm to patients up to a desired level, to optimize cancer treatment without fatally harming the patient (e.g., up to a desired or determined "safety" level, etc.). Similarly, following cancer treatment (e.g., immunotherapy), the systems and methods described herein can be used to optimize one or more recovery treatments or therapies.

In an example, if a patient has an existing cardiac monitor or ambulatory medical device, the existing devices may switch modes to implement the systems and methods described herein. In other examples, one or more additional ambulatory medical devices can be deployed to perform the systems and methods described herein.

Figure 2:
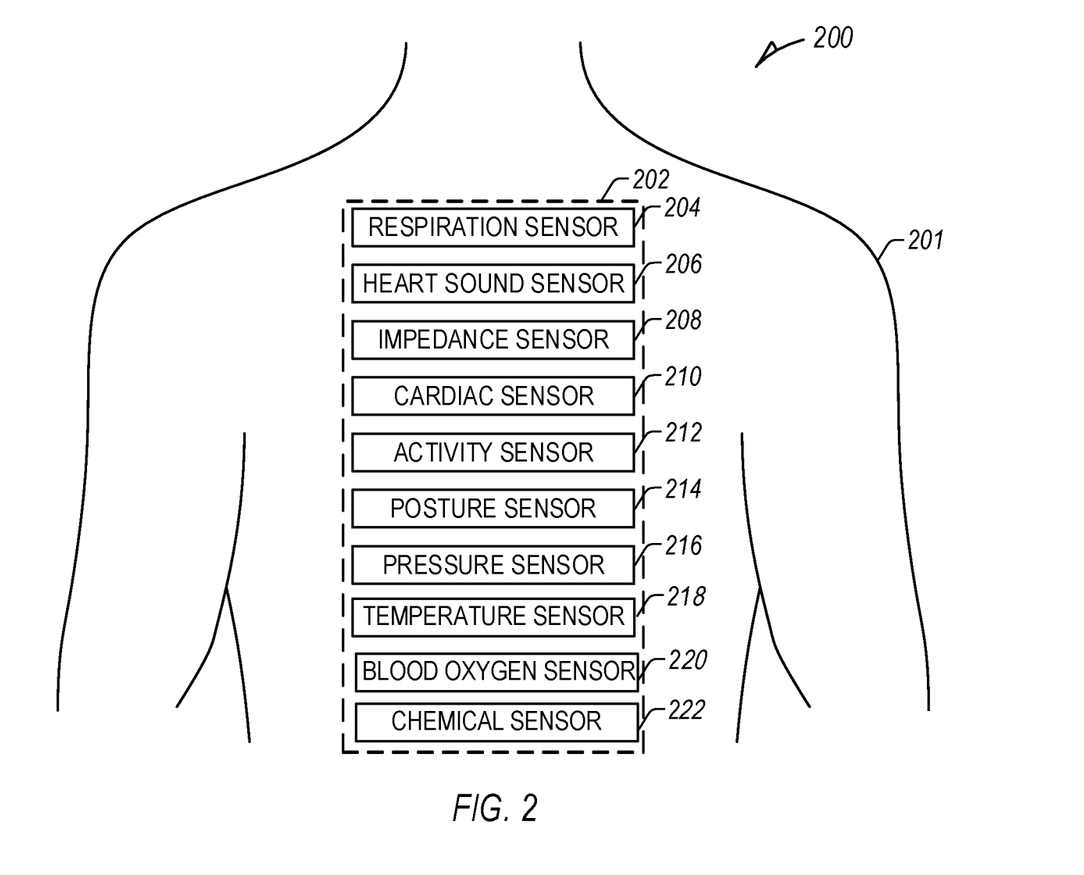
FIG. 2 illustrates an example system including an ambulatory medical device (AMD) configured to sense or detect information from a patient.

FIG. 2 illustrates an example system 200 including an ambulatory medical device (AMD) 202 configured to sense or detect information from a patient 201. In an example, the AMD 202 can include an implantable medical device (IMD), a subcutaneous or leadless medical device, a wearable or external medical device, or one or more other implantable or external medical devices or patient monitors.

The AMD 202 can include a single device, or a plurality of medical devices or monitors configured to detect patient information.

The AMD 202 can include one or more sensors configured to receive physiologic information of a patient 201. The received physiologic information may include sensor measurements indicative of particular medical conditions, patient signs or symptoms, or other physiologic responses to immunotherapy toxicity (e.g., respiratory, cardiovascular, renal, hepatic, neurologic, inflammatory, and constitutional responses, skin conditions, and coagulation). In an example, the AMD 202 can include one or more physiologic sensors, such as a respiration sensor 204, a heart sound sensor 206, an impedance sensor 208, a cardiac sensor 210, an activity sensor 212, a posture sensor 214, a pressure sensor 216, a temperature sensor 218, a blood oxygen sensor 220, and a chemical sensor 222. The respiration sensor 204 can be configured to receive respiration information, including but not limited to a respiration rate (RR), a respiration volume (tidal volume), an RSBI, indicators of dyspnea, tachypnea, etc. Such respiration information may be used to detect respiratory toxicity of the immunotherapy, such as pulmonary edema, dyspnea, and pneumonitis, among others.

The heart sound sensor 206 may take a form of an accelerometer or a microphone sensor, and can be configured to receive heart sound information, including but not limited to intensity (e.g., amplitudes) one or more of S1, S2, S3, or S4 heart sound components, and timing parameters such as systolic timing intervals measured using the heart sound components. Such heart sounds information may be used to detect cardiotoxicity and cardiopulmonary toxicity of the immunotherapy, such as deterioration in cardiac function (e.g., reduced contractility, reduced ejection fraction, reduced systolic blood pressure, increased end-diastolic volume, and reduced cardiac output), diastolic abnormalities, myocardial depression, ischemia and microvascular dysfunction, cardiac arrhythmias, and WHF, among others. For example, a decrease in S1 amplitude may indicate a reduced myocardial contractility, a decrease in S2 amplitude may indicate a reduced arterial blood pressure and cardiac output, and an increase in S3, S4, or S4/S3 ratio may indicate worsened diastolic function due to the cardiotoxicity.

The microphone or accelerometer sensor may sense physiological information other than heart sounds. In an example, a microphone may be used to sense information of patient voice, which can be further analyzed to detect patient signs or symptoms associated immunotherapy toxicity, such as malaise, fatigue, myalgia, arthralgia, nausea, headache, vomiting, diarrhea, or neurologic disorders such as metal status changes or confusion, etc. The microphone sensor may sense respiration such as respiratory rate, which may be used to detect tachypnea or other disordered breathing. An accelerometer sensor may be used to sense physical activity which may indicate fatigue, or neurologic disorders such as tremor, altered gait, or seizure, or to sense body shaking which may indicate rigor.

The impedance sensor 208 can be configured to receive impedance information (e.g., intracardiac, intrathoracic, or transthoracic impedance). A decrease in body impedance may be indicative of body fluid accumulation, such as in the lungs. Pulmonary edema may be associated with cardiopulmonary toxicity of the immunotherapy. In an example, the impedance sensor 208 may detect pulmonary edema based on a decrease in thoracic impedance. In some patients, immunotherapy may cause gastrointestinal toxicity including symptoms of vomiting and diarrhea, which may lead to intravascular dehydration. The impedance sensor 208 may detect an increase in body impedance indicative of dehydration.

The cardiac sensor 210 can be configured to receive cardiac electrical information, such as an electrocardiograph (ECG), a subcutaneous ECG, or an intracardiac electrogram (EGM). Cardiac parameters such as heart rate, heart rate variability, cardiac synchrony, cardiac arrhythmias, conduction abnormalities, may be generated and used to detect cardiotoxicity of immunotherapy, such as development supraventricular or ventricular arrhythmias.

The activity sensor 212 can be configured to receive information about a physical motion (e.g., activity, steps, etc.), and the posture sensor 214 can be configured to receive posture or position information. Changes in physical activity or changes in posture may be indicative of acute toxicity post immunotherapy, or patient habitual change secondary to toxicity such as development or worsening of heart failure. The physical activity or motion information and the posture or position information may additionally or alternatively be used to trigger one or more other physiologic sensors, such as heart sounds, impedance, or pressure data acquired under a specified physical activity level or a specified posture.

The pressure sensor 216 may be configured to receive pressure information. In an example, the pressure sensor 216 is a blood pressure sensor configured to sense blood pressure, which may further be used to detect hypotension, a symptom of immunotherapy toxicity. In another example, the pressure sensor 216 is configured to sense abdominal pressure. Gastrointestinal toxicity of immunotherapy may be manifested by nausea, vomiting, diarrhea. Abnormal abdominal pressure detected by the pressure sensor 216 may be used to detect one or more of symptoms associated with the gastrointestinal toxicity.

The temperature sensor 218 may be configured to receive body temperature information. Examples of the body temperature sensor may be include a thermal couple, a thermistor, an infrared sensor, or a temperature sense integrated circuit. As fever is one of adverse systemic inflammatory responses to immunotherapy, a high body temperature (e.g., above 38° C.), along with other sensor information, may be indicative of immunotherapy toxicity.

The blood oxygen sensor 220 may be configured to receive information about blood oxygen saturation. In an example, the blood oxygen sensor 220 is a pulse oximeter. Immunotherapy toxicity in some patients may be manifested as hypoxia, a condition where the body or a body region is deprived of adequate oxygen supply at the tissue level. Accordingly, a low arterial blood oxygen saturation (e.g., less than 92%), along with other sensor information, may be used to detect immunotherapy toxicity.

The chemical sensor 222 may be configured to receive information of one or more blood chemicals. In an example, the chemical sensor 222 can be configured to detect a level of a liver enzyme, such as alanine aminotransferase (ALT), or aspartate aminotransferase (AST). The ALT is a liver enzyme that can convert alanine, an amino acid found in proteins, into pyruvate, an important intermediate in cellular energy production. In healthy individuals, ALT levels in the blood are low. When the liver is damaged, ALT is released into the blood, usually before more obvious signs of liver damage occur. AST level usually also rises whenever the liver is being damaged. AST/ALT ratio may be calculated to aid in distinguishing between different causes and severity of liver injury and to help distinguish liver injury from damage to heart or muscles. Immunotherapy may cause hepatic toxicity, causing liver damage. An increase in AST or ALT detected by the chemical sensor 222, when exceeding a threshold value, may be suggestive of hepatic toxicity. In some examples, the chemical sensor 222 may detect level(s) of one or more of a range of interleukins (ILs) for regulating immune responses (e.g., IL-113, IL-2, IL-5, IL-6, IL-8, IL-10, IL-13), IL-1 receptor antagonist (IL-1RA), interferons (e.g., interferon gamma, or IFNγ), C-reactive protein (CRP), ferritin, tumor necrosis factor (TNF)α, granulocyte-macrophage colony-stimulating factor (GM-CSF), monocyte chemoattractant protein-1 (MCP-1), macrophage inflammatory proteins (e.g., MIP1α), Eotaxin, fibrinogen, lactate dehydrogenase (LDH), blood urea nitrogen (BUN), creatine (Cr), or fractalkine (CX3CL1), among others. The detected level(s) of one or more of said substances may be indicative of or correlated to inflammatory, hepatic, or renal responses to immunotherapy toxicity.

In another example, the chemical sensor 222 can be configured to sense information about blood electrolyte level such as potassium, sodium, calcium, or creatinine, among others. Electrolyte imbalance may be caused by diarrhea, a common side of immunotherapy. Additionally, the blood electrolyte level, such as a low potassium level and/or a high creatinine level may be used to detect kidney dysfunction. Immunotherapy may cause renal toxicity, manifested as reduction in urine output, and other acute kidney failure symptoms. Accordingly, the blood electrolyte level, along with other sensor information, may be used to detect immunotherapy toxicity. In some examples, the chemical sensor 222 may be used to measure concentration of fibrin degradation products or fibrinogen, which may be indicative of coagulation disorders associated with immunotherapy toxicity.

The physiologic sensors as shown in FIG. 2 are by way of example and not limitation. Other physiologic sensors may similarly be used for detecting immunotherapy toxicity. In an example, a camera may be used capture a skin image which may be processed to detect skin rash, or to capture an image of hand movement which may be further analyzed to detect dysmetria, both of which may be signs of immunotherapy toxicity in some patients. In another example, a flow sensor may sense information of aortic flow, which may be used to determine changes in cardiac output indicative of immunotherapy toxicity. In yet another example, a weight scale may be used to measure body weight. Significant weight loss may be indicative of anorexia associated with immunotherapy toxicity.

Figure 3:
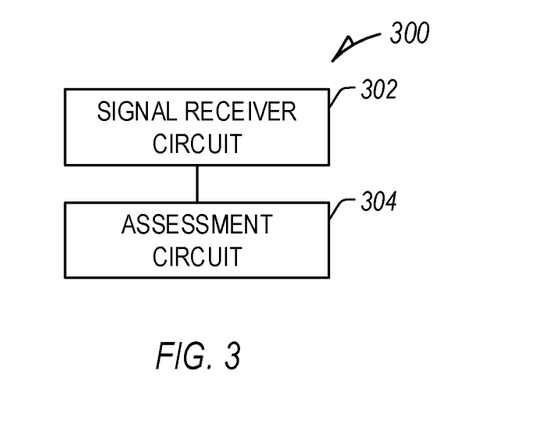
FIG. 3 illustrates an example system (e.g., a medical device, etc.) including a signal receiver circuit and an assessment circuit.

FIG. 3 illustrates an example system (e.g., a medical device, etc.) 300 including a signal receiver circuit 302 and an assessment circuit 304. The signal receiver circuit 302 can be configured to receive patient information, such as physiologic information of a patient (or group of patients) from one or more of the physiologic sensors 204-222 as discussed above with reference to FIG. 2. The assessment circuit 304 can be configured to receive information from the signal receiver circuit 302 in response an immunotherapy for cancer treatment (e.g., CAR T-cell therapy), determine an indication of toxicity using the received physiologic information, and determine one or more diagnostic or therapeutic parameters (e.g., composite physiologic parameters, stratifiers, one or more pacing parameters, etc.), such as described herein. In an example, the assessment circuit can determine an optimized therapy delivery parameter using the indication of toxicity, such as drug type, dosage, or timing of the drug therapy. In an example, the assessment circuit 304 can generate a composite risk score using the received physiologic information, and to determine the indication of toxicity using the composite risk score. The composite risk score can be a linear or a nonlinear combination (e.g., weighted combination) of the received physiologic information from the two or more sensors.

The assessment circuit 304 can be configured to provide an output to a user, such as to a display or one or more other user interface, the output including a score, a trend, or other indication. In other examples, the assessment circuit 304 can be configured to provide an output to another circuit, machine, or process, such as to control, adjust, or cease a therapy of a medical device, a drug delivery system, etc.

Figure 4:
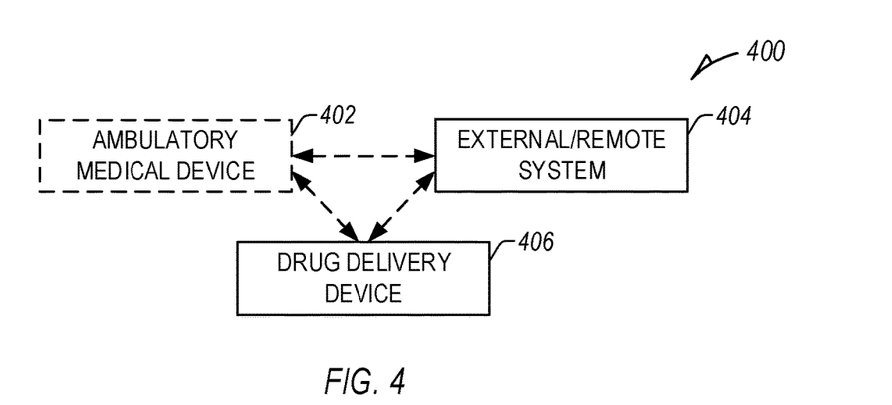
FIG. 4 illustrates an example system including an ambulatory medical device (AMD) coupled to an external or remote system, such as an external programmer.

FIG. 4 illustrates an example system 400 including an ambulatory medical device (AMD) 402 coupled to an external or remote system 404, such as an external programmer, and a drug delivery device 406. The AMD 402 can be an implantable device, an external device, or a combination or permutation of one or more implantable or external devices. In an example, one or more of the signal receiver circuit 302 or the assessment circuit 304 can be located in the AMD 402, or the remote system 404. In an example, the AMD 402 can include a stimulation circuit configured to generate an electrostimulation therapy (e.g., pacing or defibrillation pulses) to be provided to a patient. The remote system 404 can include a specialized device configured to interact with the AMD 402, including to program or receive information from the AMD 402. One or more of the AMD 402 or the remote system 404 may determine a toxicity index (e.g., the composite risk score) using the received physiologic information, and compare the determined toxicity index to a threshold. In response to the determined toxicity index exceeding the threshold, the AMD 402 or the remote system 404 may adjust the therapy parameter using the determined toxicity index. The stimulation circuit in the AMD 402 may generate and deliver electrostimulation therapy to a patient according to the adjusted therapy parameter.

The drug delivery device 406 can be configured to send information to or receive information from one or both of the AMD 402 or the remote system 404. The drug delivery device 406 can be configured to deliver one or more drugs to a patient. In an example, the delivered drug may include CAR T-cells as immunotherapy agents for cancer treatment. In another example, the delivered drug may include antitoxicity drug that may alleviate the symptoms, inflammation, or other adverse effects of the immunotherapy. In an example, the AMD 402 or the remote system 404 can be configured to control one or more parameters of the drug delivery system 406, such as drug type, dosage, or timing of the drug therapy, using the toxicity index generated from the received physiologic information.

Figure 5:
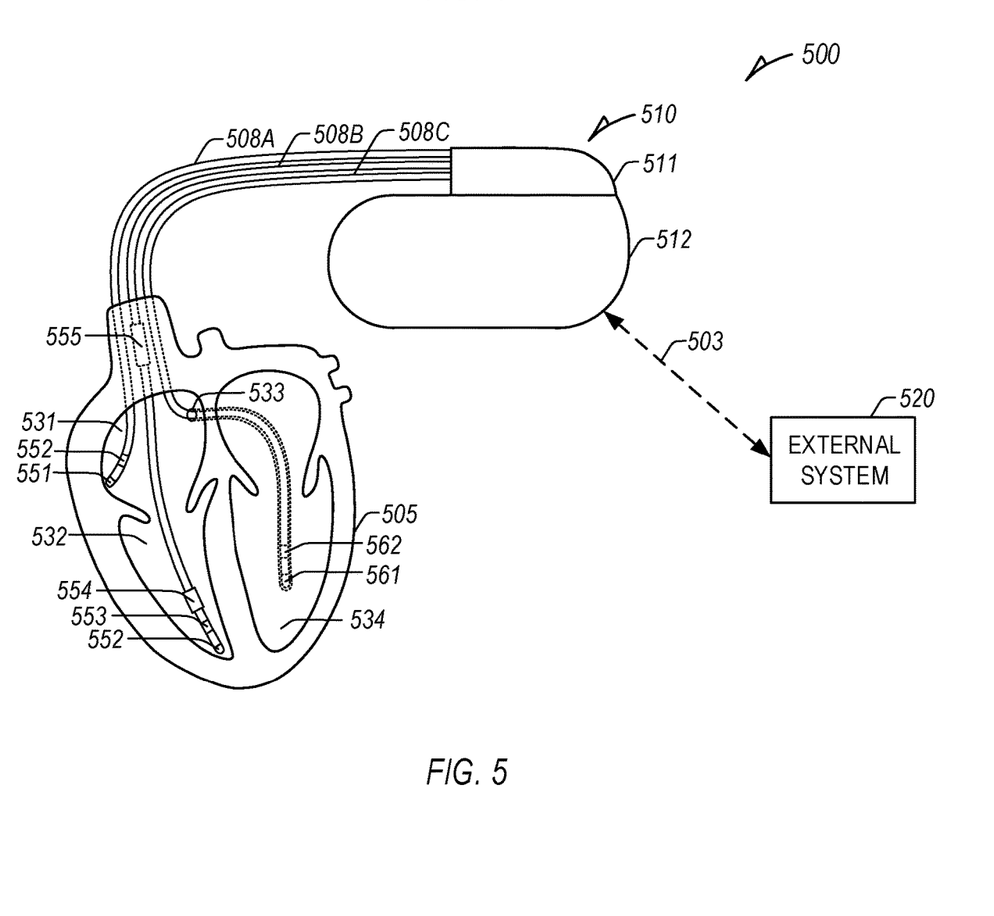
FIG. 5 illustrates an example of a Cardiac Rhythm Management (CRM) system and portions of an environment in which the CRM system can operate.

FIG. 5 illustrates an example of a Cardiac Rhythm Management (CRM) system 500 and portions of an environment in which the CRM system 500 can operate. The CRM system 500 can include an ambulatory medical device, such as an implantable medical device (IMD) 510 that can be electrically coupled to a heart 505 such as through one or more leads 508A-C coupled to the IMD 510 using a header 511, and an external system 520 that can communicate with the IMD 510 such as via a communication link 503. The 1 MB 510 may include an implantable cardiac device such as a pacemaker, an implantable cardioverter-defibrillator (ICD), or a cardiac resynchronization therapy defibrillator (CRT-D). The IMD 510 can include one or more monitoring or therapeutic devices such as a subcutaneously implanted device, a wearable external device, a neural stimulator, a drug delivery device, a biological therapy device, or one or more other ambulatory medical devices. The 1 MB 510 may be coupled to, or may be substituted by a monitoring medical device such as a bedside or other external monitor.

The 1 MB 510 can include a hermetically sealed can 512 that can house an electronic circuit that can sense a physiologic signal in the heart 505 and can deliver one or more therapeutic electrical pulses to a target region, such as in the heart, such as through one or more leads 508A-C. In certain examples, the CRM system 500 can include only a single lead, such as 508B, or can include only two leads, such as 508A and 508B.

The lead 508A can include a proximal end that can be configured to be connected to IMD 510 and a distal end that can be configured to be placed at a target location such as in the right atrium (RA) 531 of the heart 505. The lead 508A can have a first pacing-sensing electrode 551 that can be located at or near its distal end, and a second pacing-sensing electrode 552 that can be located at or near the electrode 551. The electrodes 551 and 552 can be electrically connected to the IMD 510 such as via separate conductors in the lead 508A, such as to allow for sensing of the right atrial activity and optional delivery of atrial pacing pulses. The lead 508B can be a defibrillation lead that can include a proximal end that can be connected to IMD 510 and a distal end that can be placed at a target location such as in the right ventricle (RV) 532 of heart 505. The lead 508B can have a first pacing-sensing electrode 552 that can be located at distal end, a second pacing-sensing electrode 553 that can be located near the electrode 552, a first defibrillation coil electrode 554 that can be located near the electrode 553, and a second defibrillation coil electrode 555 that can be located at a distance from the distal end such as for superior vena cava (SVC) placement. The electrodes 552 through 555 can be electrically connected to the IMD 510 such as via separate conductors in the lead 508B. The electrodes 552 and 553 can allow for sensing of a ventricular electrogram and can optionally allow delivery of one or more ventricular pacing pulses, and electrodes 554 and 555 can allow for delivery of one or more ventricular cardioversion/defibrillation pulses. In an example, the lead 508B can include only three electrodes 552, 554 and 555. The electrodes 552 and 554 can be used for sensing or delivery of one or more ventricular pacing pulses, and the electrodes 554 and 555 can be used for delivery of one or more ventricular cardioversion or defibrillation pulses. The lead 508C can include a proximal end that can be connected to the IMD 510 and a distal end that can be configured to be placed at a target location such as in a left ventricle (LV) 534 of the heart 505. The lead 508C may be implanted through the coronary sinus 533 and may be placed in a coronary vein over the LV such as to allow for delivery of one or more pacing pulses to the LV. The lead 508C can include an electrode 561 that can be located at a distal end of the lead 508C and another electrode 562 that can be located near the electrode 561. The electrodes 561 and 562 can be electrically connected to the IMD 510 such as via separate conductors in the lead 508C such as to allow for sensing of the LV electrogram and optionally allow delivery of one or more resynchronization pacing pulses from the LV.

The IMD 510 can include an electronic circuit that can sense a physiologic signal, such as via one or more of the physiologic sensors 204-222 as discussed above with reference to FIG. 2. In an example, the physiologic signal can include an electrogram or a signal representing mechanical function of the heart 505. The hermetically sealed can 512 may function as an electrode such as for sensing or pulse delivery. For example, an electrode from one or more of the leads 508A-C may be used together with the can 512 such as for unipolar sensing of an electrogram or for delivering one or more pacing pulses. A defibrillation electrode from the lead 508B may be used together with the can 512 such as for delivering one or more cardioversion/defibrillation pulses. In an example, the 1 MB 510 can sense impedance such as between electrodes located on one or more of the leads 508A-C or the can 512. The IMD 510 can be configured to inject current between a pair of electrodes, sense the resultant voltage between the same or different pair of electrodes, and determine impedance using Ohm's Law. The impedance can be sensed in a bipolar configuration in which the same pair of electrodes can be used for injecting current and sensing voltage, a tripolar configuration in which the pair of electrodes for current injection and the pair of electrodes for voltage sensing can share a common electrode, or tetrapolar configuration in which the electrodes used for current injection can be distinct from the electrodes used for voltage sensing. In an example, the IMD 510 can be configured to inject current between an electrode on the RV lead 508B and the can 512, and to sense the resultant voltage between the same electrodes or between a different electrode on the RV lead 508B and the can 512. A physiologic signal can be sensed from one or more physiologic sensors that can be integrated within the 1 MB 510. The 1 MB 510 can also be configured to sense a physiologic signal from one or more external physiologic sensors or one or more external electrodes that can be coupled to the IMD 510. Examples of the physiologic signal can include one or more of heart rate, heart rate variability, intrathoracic impedance, intracardiac impedance, arterial pressure, pulmonary artery pressure, RV pressure, LV coronary pressure, coronary blood temperature, blood oxygen saturation, one or more heart sounds, physical activity or exertion level, physiologic response to activity, posture, respiration, body weight, or body temperature.

The arrangement and functions of these leads and electrodes are described above by way of example and not by way of limitation. Depending on the need of the patient and the capability of the implantable device, other arrangements and uses of these leads and electrodes are.

The CRM system 500 can include a patient chronic condition-based HF assessment circuit, such as illustrated in the commonly assigned Qi An et al., U.S. application Ser. No. 14/55,392, incorporated herein by reference in its entirety. The patient chronic condition-based HF assessment circuit can include a signal analyzer circuit and a risk stratification circuit. The signal analyzer circuit can receive patient chronic condition indicators and one or more physiologic signals from the patient, and select one or more patient-specific sensor signals or signal metrics from the physiologic signals. The signal analyzer circuit can receive the physiologic signals from the patient using the electrodes on one or more of the leads 508A-C, or physiologic sensors deployed on or within the patient and communicated with the IMD 510. The risk stratification circuit can generate a composite risk index indicative of the probability of the patient later developing an event of worsening of HF (e.g., an HF decompensation event) such as using the selected patient-specific sensor signals or signal metrics. The HF decompensation event can include one or more early precursors of an HF decompensation episode, or an event indicative of HF progression such as recovery or worsening of HF status.

The external system 520 can allow for programming of the 1 MB 510 and can receives information about one or more signals acquired by IMD 510, such as can be received via a communication link 503. The external system 520 can include a local external 1 MB programmer. The external system 520 can include a remote patient management system that can monitor patient status or adjust one or more therapies such as from a remote location.

The communication link 503 can include one or more of an inductive telemetry link, a radio-frequency telemetry link, or a telecommunication link, such as an internet connection. The communication link 503 can provide for data transmission between the 1 MB 510 and the external system 520. The transmitted data can include, for example, real-time physiologic data acquired by the IMD 510, physiologic data acquired by and stored in the IMD 510, therapy history data or data indicating IMD operational status stored in the IMD 510, one or more programming instructions to the IMD 510 such as to configure the IMD 510 to perform one or more actions that can include physiologic data acquisition such as using programmably specifiable sensing electrodes and configuration, device self-diagnostic test, or delivery of one or more therapies.

The patient chronic condition-based HF assessment circuit, or other assessment circuit, may be implemented at the external system 520, which can be configured to perform HF risk stratification such as using data extracted from the 1 MB 510 or data stored in a memory within the external system 520. Portions of patient chronic condition-based HF or other assessment circuit may be distributed between the IMD 510 and the external system 520.

Portions of the IMD 510 or the external system 520 can be implemented using hardware, software, or any combination of hardware and software. Portions of the IMD 510 or the external system 520 may be implemented using an application-specific circuit that can be constructed or configured to perform one or more particular functions, or can be implemented using a general-purpose circuit that can be programmed or otherwise configured to perform one or more particular functions. Such a general-purpose circuit can include a microprocessor or a portion thereof, a microcontroller or a portion thereof, or a programmable logic circuit, or a portion thereof. For example, a "comparator" can include, among other things, an electronic circuit comparator that can be constructed to perform the specific function of a comparison between two signals or the comparator can be implemented as a portion of a general-purpose circuit that can be driven by a code instructing a portion of the general-purpose circuit to perform a comparison between the two signals. While described with reference to the IMD 510, the CRM system 500 could include a subcutaneous medical device (e.g., subcutaneous ICD, subcutaneous diagnostic device), wearable medical devices (e.g., patch based sensing device), or other external medical devices.

Figure 6:
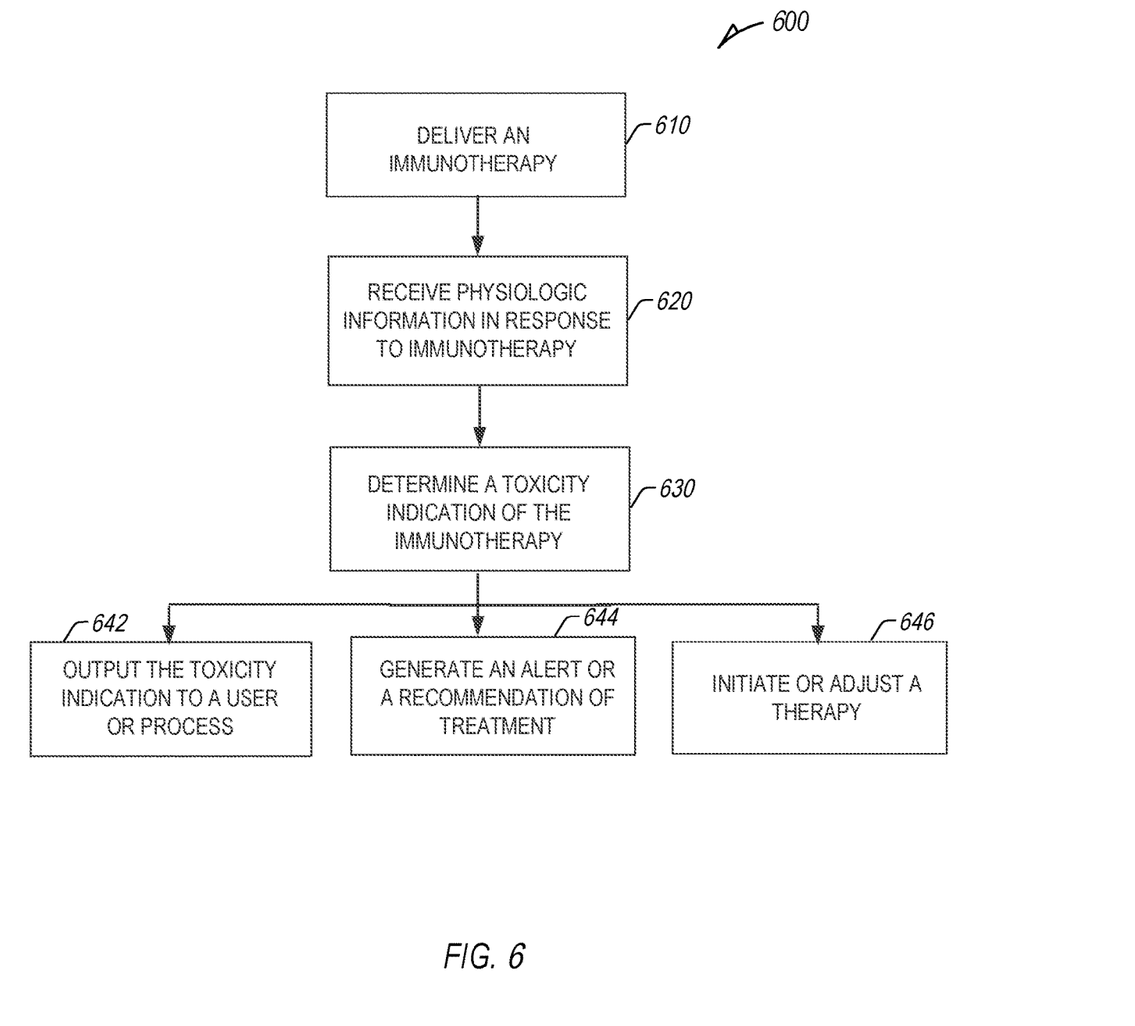
FIG. 6 illustrates an example of a method of monitoring and assessing immunotherapy toxicity in cancer patient.

FIG. 6 illustrates generally an example of a method 600 of monitoring and assessing immunotherapy toxicity in cancer patient, such as immune-mediated toxicities caused by CAR T-cell therapy. The method 600 may be implemented and executed in an ambulatory medical device such as an implantable or wearable medical device, or in a remote patient management system. In an example, the method 600 may be implemented in and executed by the AMD 202, the cancer treatment system 400, or the IMD 510. The method 600 may be used to assess multi-organ inflammatory responses to immunotherapies and the degree of toxic damages.

The method 600 commences at 610, where an immunotherapy may be delivered to a patient, such as such as infusion of re-engineered CAR T-cells that can boost the cancer-killing effects in patient's immune system, also known as CAR T-cell therapy. In response to the immunotherapy, physiologic information may be received from the patient, such as using one or more physiologic sensors. Such physiologic information may be indicative of or correlated to inflammatory responses, symptoms, or conditions of toxicity caused by or secondary to the immunotherapy. By way of non-limiting example and as described above with reference to FIG. 2, the physiologic information may include respiration information (e.g., respiration rate, tidal volume, RSBI, dyspnea or tachypnea, etc.) such as sensed by the respiration sensor 204, heart sound information (e.g., intensity or timing measurements of one or more of S1, S2, S3, or S4 heart sound components, or composite HS metrics such as a S3/S4 ratio) such as sensed by the heart sound sensor 206, impedance information (e.g., intracardiac, intrathoracic, or transthoracic impedance) such as sensed by the impedance sensor 208, cardiac electrical information (e.g., ECG, EGM, heart rate, heart rate variability, cardiac arrhythmias, etc.) such as sensed by the cardiac sensor 210, physical activity and motion information such as sensed by the activity sensor 212, posture or position information such as sensed by the posture sensor 214, pressure information (e.g., blood pressure, abdominal pressure) such as sensed by pressure sensor 216, body temperature information such as sensed by temperature sensor 218, blood oxygen saturation information such as sensed by the blood oxygen sensor 220, blood chemical information (e.g., liver enzyme such as ALT or AST, blood electrolyte such as potassium, sodium, calcium, or creatinine) such as detected by the chemical sensor 222, among others. The physiologic information sensed from each sensor, individually or in combination with other sensor information, may be used detect one or more of cardiac, respiratory, neurologic, hematologic, gastrointestinal, hepatic, or renal toxicities associated with the immunotherapy, such as CAR T-cell therapy, as discussed above with reference to FIG. 2.

At 630, an indication of immunotherapy toxicity of the may be determined using the received physiologic information, such as using the assessment circuit 304. One or more diagnostic or therapeutic parameters (e.g., composite physiologic parameters, stratifiers, one or more pacing parameters, etc.) may be generated using the received physiologic information. In an example, an optimized therapy delivery parameter may be determined using the toxicity indication, such as drug type, dosage, or timing of the drug therapy. In an example, an acute toxicity index can be generated using a composite of physiologic information acquired by two or more physiologic sensors. The composite includes a linear or a nonlinear combination (e.g., weighted combination) of the received physiologic information. The acute toxicity index may be compared to a threshold, and the immunotherapy toxicity indication may be determined in response to the acute toxicity index exceeding the threshold.

The determined toxicity indication may be used in one or more of the processes 642, 644, or 646. At 642, the toxicity indication may be output to a user or a process, such as being displayed on a display unit of a user interface included in the external or remote system 404 or the external system 520. Other information, including at least portions of the received physiologic information, features or metrics generated from the received physiologic information, and patient symptoms and information about toxicity manifestation may also be provided to the user (e.g., a clinician).

At 644, an alert or a recommendation for treatment may be generated and provided to the user. The recommendation may include one or more of further diagnostic tests to be performed, intervention or therapy optimization (e.g., dosage or timing change, change in prescribed drug, etc.), among others. At 666, intervention or therapy may be initiated or adjusted based on the toxicity indication. The therapy may include drug therapy, such as immunotherapy (e.g., CAR T-cell infusion). In another example, the therapy includes anti-toxicity drug to alleviate symptoms, inflammation, or other adverse effects of the immunotherapy. The therapy may be delivered using a drug delivery system, such as the drug delivery device 406. In an example, an optimized delivery parameter may be determined using the toxicity indication, and a cancer drug (e.g., CAR T-cell or other immunotherapy agents) may be delivered according to the optimized delivery parameter. Additionally or alternatively, the therapy may include electrical therapy, such as electrostimulation therapy (e.g., pacing or defibrillation pulses), which may be provided by the AMID 402 or the IMD 510. An optimized electrostimulation parameter may be determined using the toxicity indication, and electrostimulation therapy may be delivered to a patient according to the optimized electrostimulation parameter.

Figure 7:
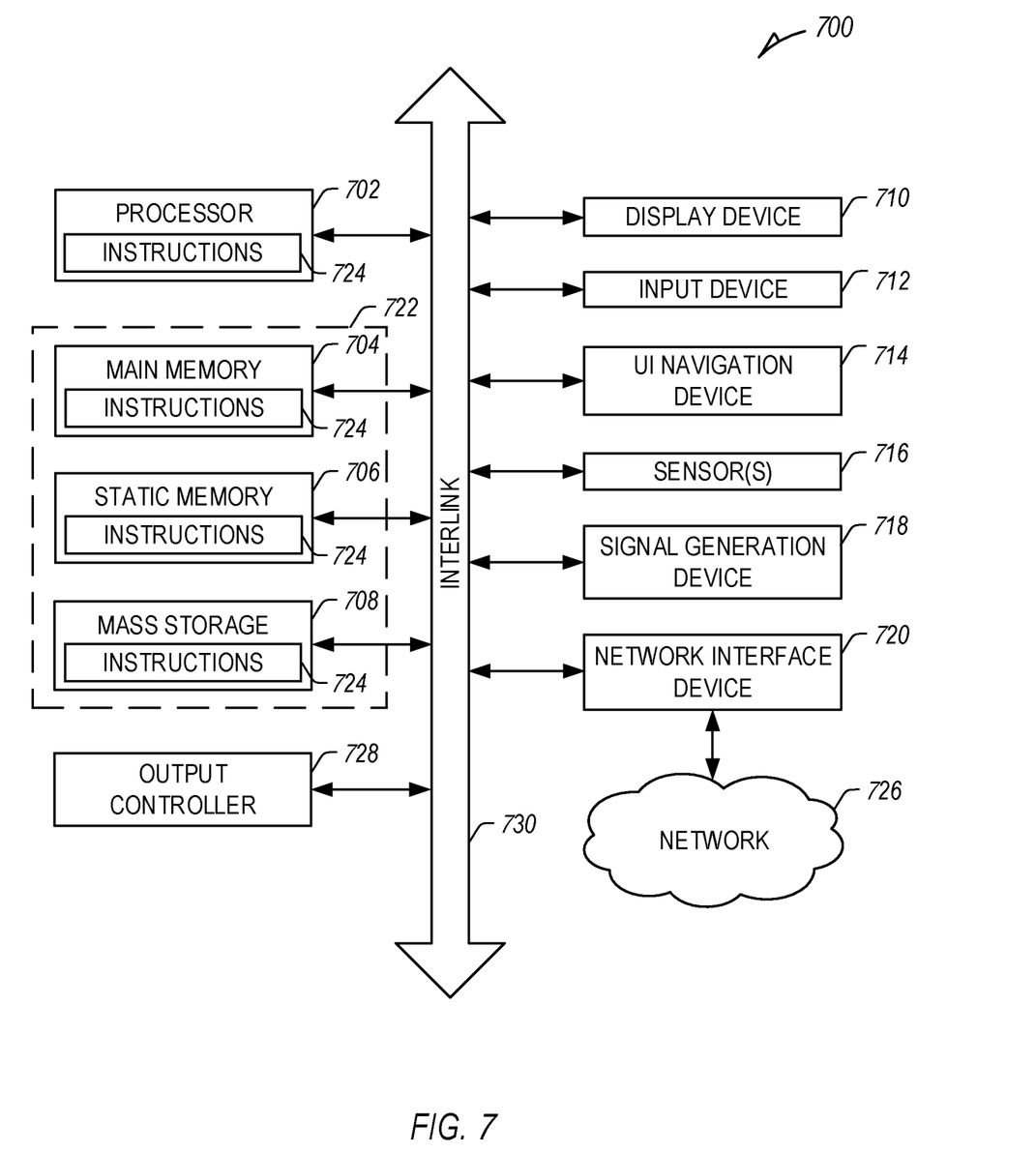
FIG. 7 illustrates a block diagram of an example machine upon which any one or more of the techniques (e.g., methodologies) discussed herein may perform.

FIG. 7 illustrates a block diagram of an example machine 700 upon which any one or more of the techniques (e.g., methodologies) discussed herein may perform. Portions of this description may apply to the computing framework of one or more of the medical devices described herein, such as the IMD, the external programmer, etc.

Examples, as described herein, may include, or may operate by, logic or a number of components, or mechanisms in the machine 700. Circuitry (e.g., processing circuitry) is a collection of circuits implemented in tangible entities of the machine 700 that include hardware (e.g., simple circuits, gates, logic, etc.). Circuitry membership may be flexible over time. Circuitries include members that may, alone or in combination, perform specified operations when operating. In an example, hardware of the circuitry may be immutably designed to carry out a specific operation (e.g., hardwired). In an example, the hardware of the circuitry may include variably connected physical components (e.g., execution units, transistors, simple circuits, etc.) including a machine-readable medium physically modified (e.g., magnetically, electrically, moveable placement of invariant massed particles, etc.) to encode instructions of the specific operation. In connecting the physical components, the underlying electrical properties of a hardware constituent are changed, for example, from an insulator to a conductor or vice versa. The instructions enable embedded hardware (e.g., the execution units or a loading mechanism) to create members of the circuitry in hardware via the variable connections to carry out portions of the specific operation when in operation. Accordingly, in an example, the machine-readable medium elements are part of the circuitry or are communicatively coupled to the other components of the circuitry when the device is operating. In an example, any of the physical components may be used in more than one member of more than one circuitry. For example, under operation, execution units may be used in a first circuit of a first circuitry at one point in time and reused by a second circuit in the first circuitry, or by a third circuit in a second circuitry at a different time. Additional examples of these components with respect to the machine 700 follow.

In alternative embodiments, the machine 700 may operate as a standalone device or may be connected (e.g., networked) to other machines. In a networked deployment, the machine 700 may operate in the capacity of a server machine, a client machine, or both in server-client network environments. In an example, the machine 700 may act as a peer machine in peer-to-peer (P2P) (or other distributed) network environment. The machine 700 may be a personal computer (PC), a tablet PC, a set-top box (STB), a personal digital assistant (PDA), a mobile telephone, a web appliance, a network router, switch or bridge, or any machine capable of executing instructions (sequential or otherwise) that specify actions to be taken by that machine. Further, while only a single machine is illustrated, the term "machine" shall also be taken to include any collection of machines that individually or jointly execute a set (or multiple sets) of instructions to perform any one or more of the methodologies discussed herein, such as cloud computing, software as a service (SaaS), other computer cluster configurations.

The machine (e.g., computer system) 700 may include a hardware processor 702 (e.g., a central processing unit (CPU), a graphics processing unit (GPU), a hardware processor core, or any combination thereof), a main memory 704, a static memory (e.g., memory or storage for firmware, microcode, a basic-input-output (BIOS), unified extensible firmware interface (UEFI), etc.) 706, and mass storage 708 (e.g., hard drive, tape drive, flash storage, or other block devices) some or all of which may communicate with each other via an interlink (e.g., bus) 730. The machine 700 may further include a display unit 710, an alphanumeric input device 712 (e.g., a keyboard), and a user interface (UI) navigation device 714 (e.g., a mouse). In an example, the display unit 710, input device 712, and UI navigation device 714 may be a touch screen display. The machine 700 may additionally include a signal generation device 718 (e.g., a speaker), a network interface device 720, and one or more sensors 716, such as a global positioning system (GPS) sensor, compass, accelerometer, or one or more other sensors. The machine 700 may include an output controller 728, such as a serial (e.g., universal serial bus (USB), parallel, or other wired or wireless (e.g., infrared (IR), near field communication (NFC), etc.) connection to communicate or control one or more peripheral devices (e.g., a printer, card reader, etc.).

Registers of the processor 702, the main memory 704, the static memory 706, or the mass storage 708 may be, or include, a machine-readable medium 722 on which is stored one or more sets of data structures or instructions 724 (e.g., software) embodying or utilized by any one or more of the techniques or functions described herein. The instructions 724 may also reside, completely or at least partially, within any of registers of the processor 702, the main memory 704, the static memory 706, or the mass storage 708 during execution thereof by the machine 700. In an example, one or any combination of the hardware processor 702, the main memory 704, the static memory 706, or the mass storage 708 may constitute the machine-readable medium 722. While the machine-readable medium 722 is illustrated as a single medium, the term "machine-readable medium" may include a single medium or multiple media (e.g., a centralized or distributed database, and/or associated caches and servers) configured to store the one or more instructions 724.

The term "machine-readable medium" may include any medium that is capable of storing, encoding, or carrying instructions for execution by the machine 700 and that cause the machine 700 to perform any one or more of the techniques of the present disclosure, or that is capable of storing, encoding or carrying data structures used by or associated with such instructions. Non-limiting machine-readable medium examples may include solid-state memories, optical media, magnetic media, and signals (e.g., radio frequency signals, other photon based signals, sound signals, etc.). In an example, a non-transitory machine-readable medium comprises a machine-readable medium with a plurality of particles having invariant (e.g., rest) mass, and thus are compositions of matter. Accordingly, non-transitory machine-readable media are machine-readable media that do not include transitory propagating signals. Specific examples of non-transitory machine-readable media may include: non-volatile memory, such as semiconductor memory devices (e.g., Electrically Programmable Read-Only Memory (EPROM), Electrically Erasable Programmable Read-Only Memory (EEPROM)) and flash memory devices; magnetic disks, such as internal hard disks and removable disks; magneto-optical disks; and CD-ROM and DVD-ROM disks.

The instructions 724 may be further transmitted or received over a communications network 726 using a transmission medium via the network interface device 720 utilizing any one of a number of transfer protocols (e.g., frame relay, internet protocol (IP), transmission control protocol (TCP), user datagram protocol (UDP), hypertext transfer protocol (HTTP), etc.). Example communication networks may include a local area network (LAN), a wide area network (WAN), a packet data network (e.g., the Internet), mobile telephone networks (e.g., cellular networks), Plain Old Telephone (POTS) networks, and wireless data networks (e.g., Institute of Electrical and Electronics Engineers (IEEE) 802.11 family of standards known as Wi-Fi®, IEEE 802.16 family of standards known as WiMax®), IEEE 802.15.4 family of standards, peer-to-peer (P2P) networks, among others. In an example, the network interface device 720 may include one or more physical jacks (e.g., Ethernet, coaxial, or phone jacks) or one or more antennas to connect to the communications network 726. In an example, the network interface device 720 may include a plurality of antennas to wirelessly communicate using at least one of single-input multiple-output (SIMO), multiple-input multiple-output (MIMO), or multiple-input single-output (MISO) techniques. The term "transmission medium" shall be taken to include any intangible medium that is capable of storing, encoding or carrying instructions for execution by the machine 700, and includes digital or analog communications signals or other intangible medium to facilitate communication of such software. A transmission medium is a machine-readable medium.

Various embodiments are illustrated in the figures above. One or more features from one or more of these embodiments may be combined to form other embodiments. Method examples described herein can be machine or computer-implemented at least in part. Some examples may include a computer-readable medium or machine-readable medium encoded with instructions operable to configure an electronic device or system to perform methods as described in the above examples. An implementation of such methods can include code, such as microcode, assembly language code, a higher-level language code, or the like. Such code can include computer readable instructions for performing various methods. The code can form portions of computer program products. Further, the code can be tangibly stored on one or more volatile or non-volatile computer-readable media during execution or at other times.

The above detailed description is intended to be illustrative, and not restrictive. The scope of the disclosure should, therefore, be determined with references to the appended claims, along with the full scope of equivalents to which such claims are entitled.

What is claimed is:

1. A system comprising:
    an ambulatory medical device configured to receive physiologic information from a patient receiving immunotherapy, the received physiologic information including heart sound information of the patient; and an assessment circuit configured to determine a toxicity indication associated with the immunotherapy using changes in the received heart sound information.

2. The system of claim 1, comprising a drug delivery system configured to control delivery of the immunotherapy to the patient according to a delivery parameter, wherein the immunotherapy includes a chimeric antigen receptor (CAR) T-cell therapy, and the assessment circuit is configured to determine an optimized delivery parameter for delivering the immunotherapy using the determined toxicity indication.

3. The system of claim 2, wherein the delivery parameter includes at least one of a dosage, a timing, or a drug.

4. The system of claim 1, wherein the assessment circuit is configured to provide an alert to a user using the determined toxicity indication.

5. The system of claim 1, comprising a therapy circuit configured to control a therapy to the patient according to a therapy parameter, wherein the assessment circuit is configured to adjust the therapy parameter using the determined toxicity indication.

6. The system of claim 5, wherein the assessment circuit is configured to:

determine an acute toxicity index for the patient using the changes in the received heart sound information;

compare the determined acute toxicity index to a threshold; and in response to the determined acute toxicity index exceeding the threshold, adjust the therapy parameter using the determined acute toxicity index.

7. The system of claim 1, wherein the ambulatory medical device includes a cardiac sensor configured to receive cardiac electrical or mechanical information of the patient, wherein the assessment circuit is configured to determine the toxicity indication using the received cardiac electrical or mechanical information.

8. The system of claim 1, wherein the ambulatory medical device includes a heart sound sensor configured to receive the heart sound information of the patient.

9. The system of claim 8, wherein the changes in the received heart sound information include one or more of a decrease in first heart sound (S1) amplitude, a decrease in second heart sound (S2) amplitude, or an increase in third (S3) or fourth (S4) heart sound amplitude.

10. The system of claim 1, wherein the assessment circuit is configured to determine the toxicity indication further using an increase in a systolic time interval.

11. The system of claim 1, wherein the ambulatory medical device includes a respiratory sensor configured to receive respiration information of the patient, wherein the assessment circuit is configured to determine the toxicity indication further using the received respiration information.

12. The system of claim 1, wherein the ambulatory medical device includes a chemical sensor configured to receive blood chemical information, wherein the assessment circuit is configured to detect renal or hepatic dysfunction, and to determine the toxicity indication further using the detected renal or hepatic dysfunction.

13. The system of claim 1, wherein the assessment circuit is configured to:

generate a composite risk score using the received physiologic information respectively received from two or more physiologic sensors; and determine the toxicity indication using the composite risk score.

14. A method comprising:

receiving, via an ambulatory medical device, physiologic information from a patient receiving immunotherapy, the received physiologic information including heart sound information of the patient; and determining, via an assessment circuit, a toxicity indication associated with the immunotherapy using changes in the received heart sound information.

15. The method of claim 14, comprising:

determining, via the assessment circuit, an optimized delivery parameter for delivering the immunotherapy using the determined toxicity indication; and delivering the immunotherapy to the patient according to the determined optimized delivery parameter.

16. The method of claim 15, wherein the delivery parameter includes at least one of a dosage, a timing, or a drug.

17. The method of claim 14, comprising initiating or adjusting an electrostimulation therapy using the determined toxicity indication.

18. The method of claim 14, comprising, via the assessment circuit:

determining an acute toxicity index for the patient using the changes in the received heart sound information;

comparing the determined acute toxicity index to a threshold; and in response to the determined acute toxicity index exceeding the threshold, adjusting a therapy parameter using the determined acute toxicity index.

19. The method of claim 14, wherein the assessment circuit is configured to determine the toxicity indication further using one or more of:

cardiac information;
respiration information;
body temperature information;
blood oxygen saturation information; or
blood chemical information.

20. The method of claim 14, comprising, via the assessment circuit:

generating a composite risk score using the received physiologic information respectively received from two or more physiologic sensors; and determining the toxicity indication using the composite risk score.

* * * * *